United States Patent [19]

Assmann et al.

[11] 4,413,060
[45] Nov. 1, 1983

[54] PROCESS AND APPARATUS FOR DISTRIBUTION AND PREPARATION OF SAMPLES FROM PRIMARY VESSELS

[75] Inventors: Gerd Assmann; Horst-Dietrich Helb, both of Münster, Fed. Rep. of Germany

[73] Assignee: Boehringer Ingelheim Zentrale GmbH, Fed. Rep. of Germany

[21] Appl. No.: 300,929

[22] Filed: Sep. 10, 1981

[30] Foreign Application Priority Data

Sep. 19, 1980 [DE] Fed. Rep. of Germany ....... 3035340

[51] Int. Cl.³ ...................... G01N 35/00; G01N 35/06
[52] U.S. Cl. ........................................ 436/47; 422/64; 422/65; 422/67; 422/100; 436/45
[58] Field of Search ............... 422/64, 65, 67, 100; 23/230 R

[56] References Cited

U.S. PATENT DOCUMENTS

| 4,108,602 | 8/1978 | Hanson et al. | 422/67 X |
|---|---|---|---|
| 4,115,861 | 9/1978 | Allington | 422/67 X |
| 4,138,215 | 2/1979 | Huber | 422/68 X |
| 4,166,095 | 8/1979 | Kling et al. | 422/67 |
| 4,260,580 | 4/1981 | Sindo et al. | 422/67 X |
| 4,268,477 | 5/1981 | Herzstark | 422/67 X |
| 4,287,154 | 9/1981 | Sommers | 422/67 X |

FOREIGN PATENT DOCUMENTS 2841086  3/1980  Fed. Rep. of Germany ........ 422/67

Primary Examiner—Michael S. Marcus
Attorney, Agent, or Firm—Hammond & Littell, Weissenberger and Muserlian

[57] ABSTRACT

A process and apparatus for the distribution and preparation of samples from primary vessels, especially samples of patients' sera, liquid reagents or the like, which are transferred into fixedly mounted secondary vessels of any desired construction, preferably in accordance with the data from a distribution sheet recorded by a control programing apparatus, where the secondary vessels can be moved into position one after the other by means of a transporting carriage for the primary vessel having an associated diluter, this transporting carriage being movable in the x-y plane by means of two stepping motors, and the primary vessel is brought back into its starting position after each delivery or after delivery of the samples intended for the entire series of samples.

3 Claims, 7 Drawing Figures

FIG.4
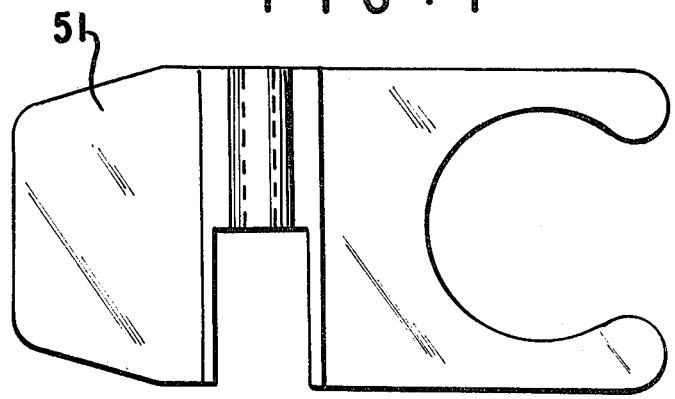
FIG.5
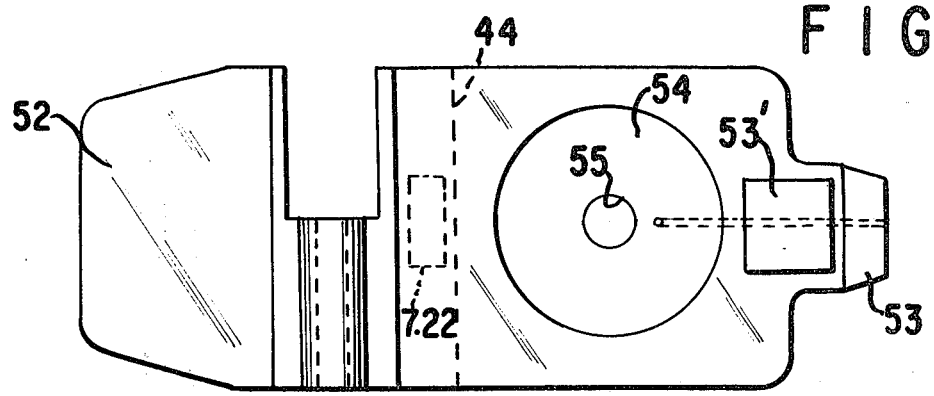
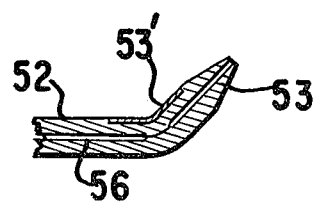
FIG.6

PROCESS AND APPARATUS FOR DISTRIBUTION AND PREPARATION OF SAMPLES FROM PRIMARY VESSELS

This invention relates to a process and apparatus for the distribution and preparation of samples from primary vessels, more particularly samples of patients' sera, liquid reagents or the like, which are transferred into fixedly mounted secondary vessels of any desired construction, preferably in accordance with the data from a distribution sheet recorded by a control programing apparatus, where the secondary vessels can be moved into position one after the other by means of a transporting carriage for the primary vessel, having an associated diluter, this transporting carriage being movable in the x-y plane by means of two stepping motors, and the primary vessel is brought back into its starting position after each delivery or after delivery of the samples intended for the entire series of samples.

THE PRIOR ART

A process and apparatus of this kind are described in German Offenlegungsschrift 2,841,086. The essential feature of this process and apparatus is that the transporting carriage is fitted with a pipette capable of being raised and lowered, and when the carriage is moved into position above the primary vessel it lowers the pipette and the sample is sucked up through a diluter connected to the pipette by movable flexible tubes and fixedly associated with the magazine, and then the pipette is raised again and moved into a delivery position determined by the control programing above a dish provided as secondary vessel, and the sample is ejected into the secondary vessel.

As a further feature of this construction, the primary vessel is formed with an electronic sensor contact and is provided with a label capable of being read by a computer, and subsequently, after laboratory preparation of the sample, the information on the label is read by means of a manually guided reading stylus and fed into the computer. The vessel labeled in this way can be brought into any desired removal position in the sample distributor, and the selected position is also fed into the computer via the sensor contact. Parallel to the identification of the sample, the requirement marking card, which is again capable of being read by a computer, is written out and given the same label marking as the primary vessel and this card is fed into the card reader connected to the computer. The sample in the primary vessel is then taken out of the primary vessel in batches, in accordance with the labeling of the vessel and the information on the requirement card, and transferred to secondary vessels arranged in accordance with the information on the card, for individual investigation (cf. DE-OS 2,841,086).

We refer also to the publication "Labtronik, Klinische Labortechnik", of Labtronik GmbH, which gives similar information to that mentioned above.

The publication refers particularly to the "Serum distributor with sample identification SV 500" having a processing capacity of more than 1000 samples per hour. The advantages of this system with regard to its safety and reliability in the preparation and identification of samples and in its throughput are widely known today. A disadvantage is the risk of contamination caused prticularly by the pipetting operation, in which traces of the samples may be left behind not only in the pipettes themselves but also, to some extent, in the connecting tube leading to the diluter, chiefly in the area going down from the pipette. Even the provision of intermediate rinsing and cleaning stages which involve taking suitable agents from a primary vessel and releasing them into a secondary vessel (which is then emptied) cannot guarantee the maximum degree of safety which is often necessary.

Moreover, the systems operating exclusively by these processes necessitate the use of primary vessels which, though of different construction, are uniform in at least one main dimension, with respect to the sensor contacts marking the position of the vessel in the sample distributor in the computer. Admittedly, this is fundamentally unavoidable with some of the high throughputs required of the sample distributor. Conversely, in many cases, it would also appear to be convenient to be able to use primary sample vessels of different dimensions and thus achieve substantial neutrality of the sample vessels, although, it should be pointed out, no rigid link with existing processes and systems is then possible.

OBJECT OF THE INVENTION

It is an object of this invention, therefore, to provide a process of the kind described hereinbefore which operates totally without contamination and which makes it possible to use vessels of different dimensions as the primary vessels (without the need for any uniform arrangement of the primary vessels in the sample distributor), but on the other hand, when vessels of identical dimensions are used, makes it possible to arrange the vessels in the sample distributors of the systems described hereinbefore.

A further object is to provide suitable apparatus for performing the process.

Other objects and advantages of the invention will become apparent as the description thereof proceeds.

DESCRIPTION OF THE INVENTION

The above objects are achieved according to the invention in that primary vessels of different dimensions filled with the sample material are arranged with their opening pointing upwards and frictionally or positively connected to a closure member adapted to fit the opening of the primary vessel but of otherwise uniform construction, the closure member comprising a pourer nozzle and an air flow aperture opening into a feed pipe, that subsequently the closure member is inserted into an intermediate carrier portion fitted with a sealable air inlet, via the air flow aperture, in the sealed position of the air inlet, that subsequently the primary vessel fitted with the intermediate carrier portion is rotated so that its opening points vertically downwards and is fixed in the clamping means of the transporting carriage (with resultant automatic opening of the air inlet, via the air flow aperture, by the intermediate carrier), that in order to release the sample material, through the diluter, air is fed into the primary vessel in a suitable amount and with a suitable tension, through a line, an intermediate carrier and the feed pipe connected to the closure member, so that a correspondingly predetermined quantity of sample material is displaced from the primary vessel, and that as the predetermined quantity of sample is delivered into a secondary vessel, by means of the diluter, air is evacuated out of the primary vessel until the surface tension of the sample material prevents any further release of this material, both when the transporting carriage is stationary and, in conjunction with the walls of the pourer nozzle, also when the carriage is moving.

The replacement of the pipetting operation by direct release of the sample material in predetermined amounts from the primary vessel into the secondary vessel and the resultant conversion of the function of the diluter into an air compressor and aspirator controlled in accordance with the quantity to be released guarantees, in conjunction with the surface tension prevailing in the primary vessel and determined by the sample material, and in conjunction with the dimensions of the pourer nozzle and the surface structure of its walls, sample distribution which is both absolutely free from contamination and also quantitatively exact. The closure member should generally be regarded as a one-way component, and in some cases is also fitted with a sensor contact which becomes effective when the primary vessel is fixed to the clamping means of the transporting carriage.

The construction of the intermediate carrier member-which may be a pair of gripping tongs opening counter to pressure, as described below, and generally having uniform dimensions-permits both simple manual fixing of the primary vessel to the clamping means of the transporting carriage, and also the use of controlled gripping means for guiding and inserting them into the clamping means, so that in this case it is possible to use the known processes described hereinbefore. Since the air inlet to the vessel is blocked when the intermediate carrier member is not inserted in the clamping means, the primary vessel is usually inserted in the clamping means of the transporting carriage with its closure member and pourer nozzle directed downwardly. The clamping means, closure member and intermediate carrier together offer considerable scope of dimensions for the construction of the primary vessel. Moreover, it is particularly easy to distribute all the samples, i.e. from the primary vessels, into the required number of secondary vessels without any interruption.

In a modified embodiment of the invention, the air supply to the primary vessel is provided directly (without the use of the intermediate carrier) via the clamping means of the transporting carriage and the closure member, and in this case the primary vessel is inserted into the clamping means of the transporting carriage in such a way that, after insertion of the primary vessel, the clamping means are pivoted manually or by a motor through 180° into the delivery position.

This embodiment of the invention generally presupposes manual fixing in the clamping means described in more detail hereinafter.

With the closure member pivoted downwards, the air supply is freed.

In a suitable apparatus for performing the process first described, the intermediate carrier member is constructed as a pair of gripping tongs opening counter to pressure, the lower portion of which, i.e. the portion pointing towards the pourer nozzle, and directed towards the closure member, has a recess for the insertion of this portion, a through opening for the passage of the pourer nozzle and an air flow aperture directed substantially at right angles to the axis of the primary vessel and to the perpendicular arm of the clamping means of the transporting carriage, while the end of the lower portion of the gripping tongs pointing towards the perpendicular arm of the clamping means of the transporting carriage is constructed as a hinged or flexible lug which is deflected upwards by a spring or other tensioning means, in the non-fixed position, and thus blocks the air flow aperture and hence the air supply, and the upper portion of the tongs is fork-shaped in construction and engages positively in its end position by means of a uniform area bounded by a shoulder and independent of the dimensions of the primary vessel.

In this end position the lug of the lower portion of the tongs is pressed downwards, i.e. substantially into a vertical position relative to the axis of the primary vessel, by a recess preferably formed in the vertical arm of the clamping means of the transporting carriage, or by guide means provided thereon, until the air supply through the air flow aperture is opened up, and this air is either guided in a continuation of this direction out of the clamping means or through the vertical arm of the clamping means to the connection for the diluter.

Particularly secure fixing is obtained if, in the open position for the air flow aperture, the lower portion of the tongs is held in this position by means of at least one magnetic connection, cooperating with a position marking means arranged in the portion of the clamping means of the transporting carriage directed at right angles to the axis of the primary vessel.

To solve the problem of sealing, the seal between the lower portion of the tongs, including the lug which provides the air connection and the closure member of the primary vessel on the one hand and the seal with the carrier of the transporting carriage on the other hand, may be provided by the at least partically elastic construction of the closure member and the lug.

It is also possible for the seal between the lower portion of the tongs, including the lug which provides the air connection, and the closure member of the primary vessel on the one hand, and the seal with the carrier of the transporting carriage on the other hand, to be formed by the provision of sealing rings between the lower portion of the tongs and the closure member and the lug and the clamping means of the transporting carriage.

In order to control the outflow, e.g. in the case of blockages, one or more carriers for receiving means for optically monitoring the outflow may be provided on the carrier of the transporting carriage, pointing in the direction of the pourer nozzle.

For performing the modified process which essentially provides for manual fixing of the primary vessels in the clamping means, without the use of an intermediate member, the apparatus is constructed so that the clamping means of the transporting carriage are constructed as gripping means for the primary vessel, into which the primary vessel can be inserted either manually or by means of program-controlled means;

the inserted portion of the closure member which engages in the horizontally guided transverse arm of the clamping means of the transporting carriage has uniform dimensions, whereas the abutment portion of the closure member directed towards the primary vessel is adapted to match the shape of the opening of the primary vessel used or is of conical shape, a hollow member which is inwardly conical in construction and capable of being clamped in the direction of the axis of the vessel engages over the base of the primary vessel, and this hollow member is guided on a transverse arm having a longitudinal guide and extending axially parallel to the longitudinal arm of the clamping means of the transporting carriage, and the primary vessel is clamped against the closure member by means of a spring, via the hollow member, in the axial direction thereof.

The process described, the possible modification thereof and the apparatus provided for performing it fully satisfy the requirements of the objects of the invention. Moreover, the process and apparatus are largely flexible so as to adapt to any desired system. The process and the apparatus also have major advantages for general operation, since the danger of spillage and evaporation is practically eliminated by the closure member.

The invention is explained more fully with reference to the accompanying drawings wherein FIG. 1 is a schematic representation of the transfer between the primary and secondary vessels.

FIG. 4 shows the upper portion of the gripping tongs.

FIG. 5 shows the lower portion of the gripping tongs with a lug formed thereon so as to open and close the air inlet.

FIG. 6 shows an enlarged view of the lug with a spring mounted therein.

Figure 1:
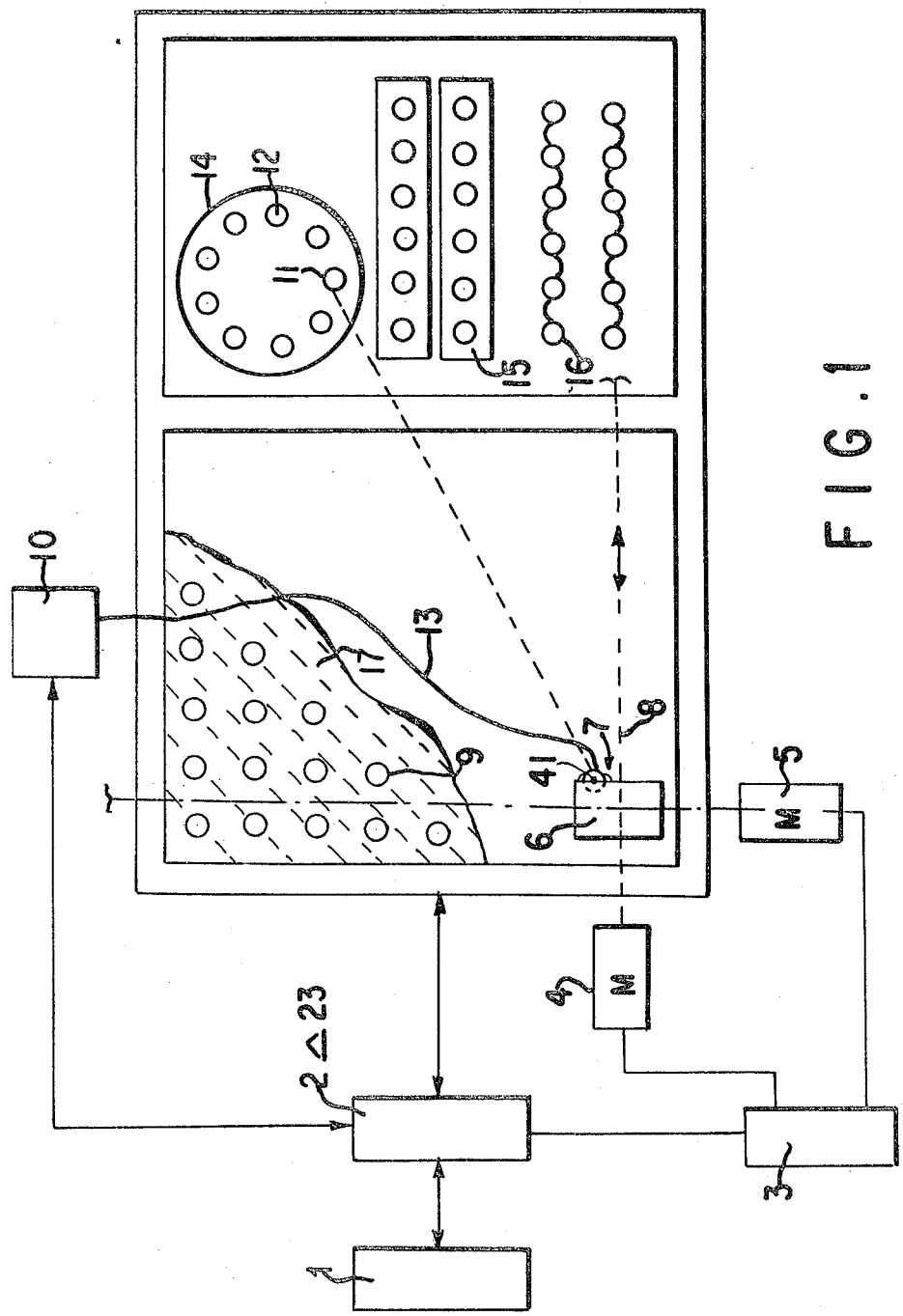
Figure 2:
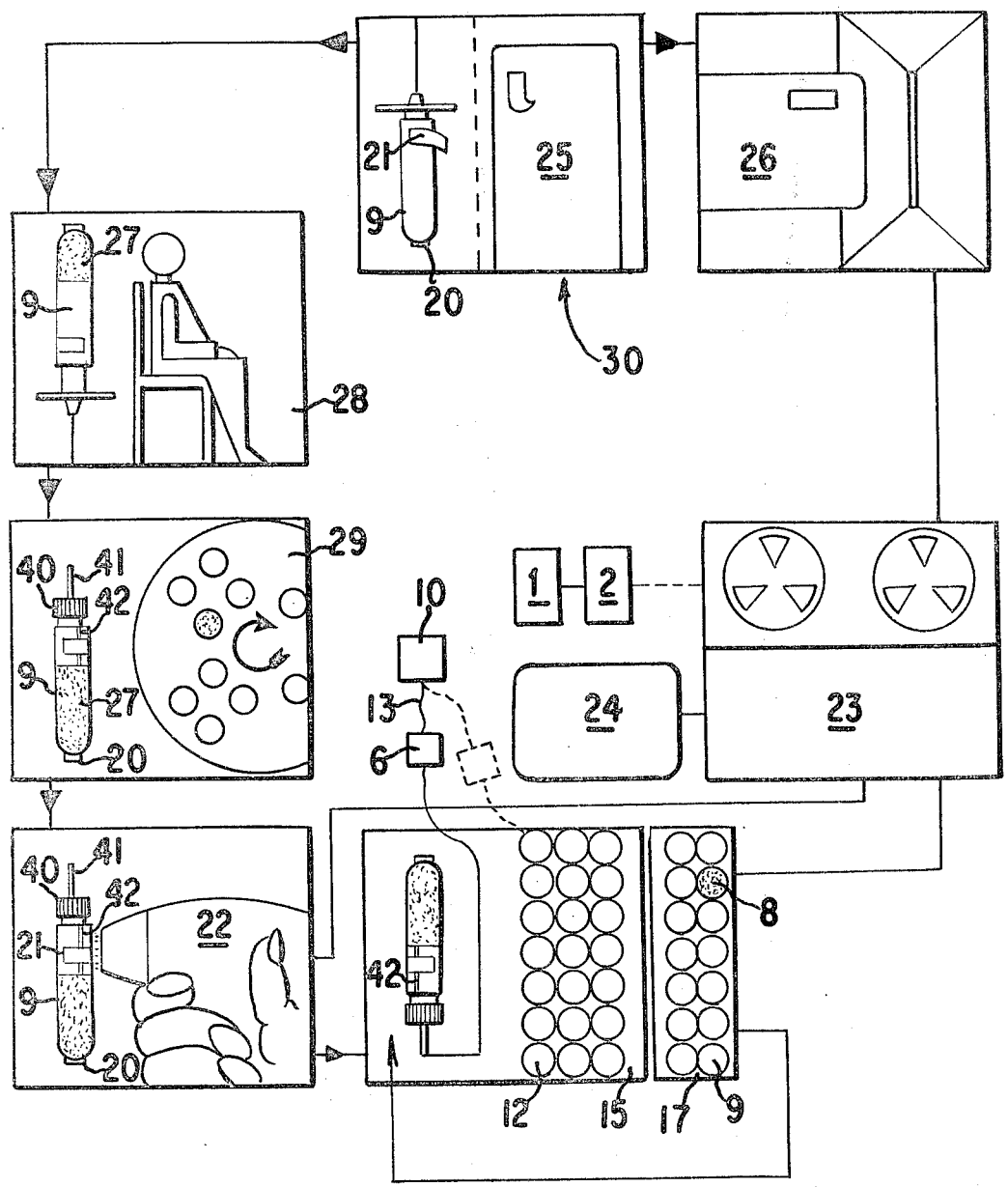
FIG. 2 shows the identification of the samples, i.e. the marking thereof and the computer-controlled associamarking of the secondary vessels with each primary vessel corresponding to the information on a reading card.

Referring to FIGS. 1 and 2, the computer 1 with associated interface 2 determines the control of coordinates 3 of the two stepping motors 4 and 5 which affect adjustment of the transporting carriage 6, provided with clamping means 7 for the primary vessel 9 in the x-y plane. In the embodiment shown, the carriage 6 is first moved into a receiving position 8 above a primary vessel 9 which is closed off by means of a closure member 40 (FIG. 2). The pourer nozzle 41 which forms part of this closure member 40 is rotated downwards, together with the primary vessel 9, manually or by means of a motor, after or during insertion into the clamping means 7 of the transporting carriage 6, so that the pourer nozzle 41 faces in the direction of the openings of the secondary vessel 12. The transporting carriage 6 then moves the primary vessel 9, which has been rotated through 180°, in the direction of the dotted arrow, into a delivery position 11 above the set position of the secondary vessel 12.

Figure 3:
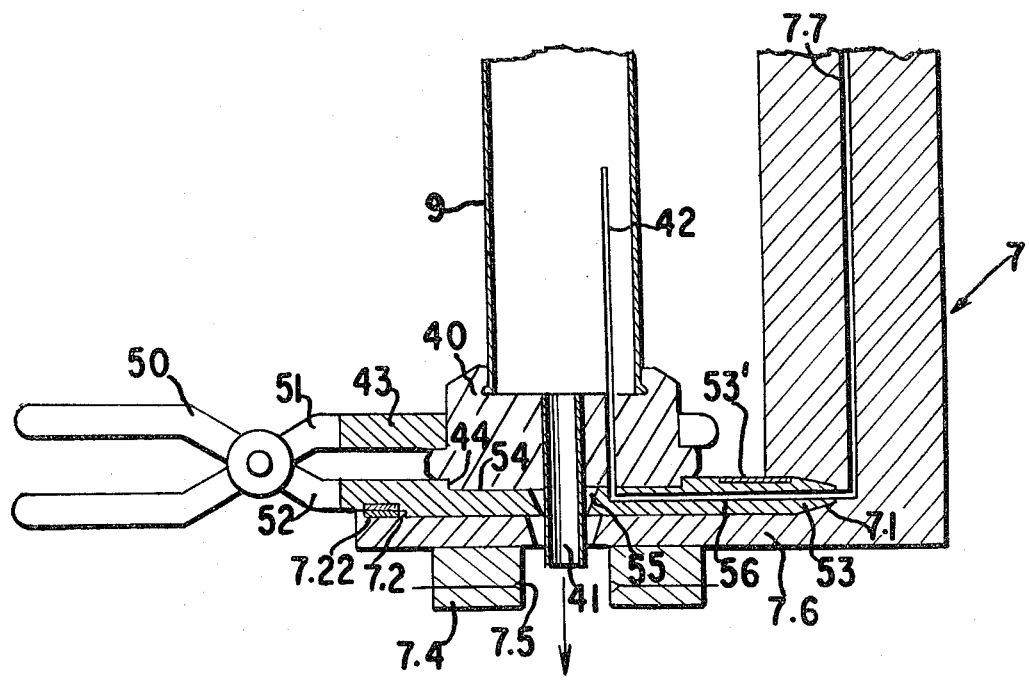
FIG. 3 shows the connection of the primary vessel, via an intermediate member in the form of gripping tongs, to the clamping means of the transporting carriage in the delivery position, i.e. with the pourer nozzle pointing downwards.

Upon opening, air is admitted in a predetermined quantity and at a predetermined pressure through the diluter 10 via the line 56 which has hitherto been closed (FIG. 3), an intermediate carrier 50 (FIG. 3) and/or the closure member 40 and a feed pipe 42 connected thereto, into the primary vessel 9 and in this way the release of the sample 27 in a predetermined amount through the pourer nozzle 41 is initiated.

If desired, liquid reagents may also be added to the sample 12 in the same way in accurately defined amounts. This ensures that already measured samples can be prepared, for example by the addition of a reagent solution to the patient's serum, and this solution may also be added automatically, i.e. controlled by the computer, and, for example, series of dilutions of any desired predetermined concentration can be prepared.

The transporting carriage 6 is connected to the diluter 10 by means of a flexible hose 13. The secondary vessels 12 are preferably mounted in round carriers 14 on the periphery thereof or in racks 15 arranged in a row one behind the other, or in chains 16, while the primary vessels 9 are housed in an exchangeable palette 17.

With regard to the sample identification shown in FIG. 2, it should be pointed out that, in the interest of clarity, the interface 2 is coordinated with the computer 23 which also takes over some comparative functions, in particular, and forms a unit therewith.

In the identification station 30, the primary vessel 9 provided with the sensor contact 20 is given a label 21 capable of being read by a computer, and the requirement marking card 25 which reveals the labeling of the primary vessel 9 and the tests to be carried out with the sample 27 in a corresponding number of secondary vessels 12 is prepared. After the sample material 27 from the patients' station 28 has been added, the primary vessel 9 thus prepared is taken to the laboratory station 29.

There, the clotted blood is generally separated from the serum by centrifuging, the sample material 27 is prepared for testing and the primary vessel 9 is sealed by means of a closure member 40, which carries the pourer nozzle 41 and feed pipe 42. The label 21 of the primary vessel 9 is then read by means of a manually guided reading stylus 22, and the information on the label is fed into the computer 23 which is connected to a display screen 24 and the primary vessel 9 is moved into the removal position 8 in the palette 17.

By means of the sensor contact 20 which becomes active at this point, the removal position 8 in the palette 17 is fed into the computer 23 so that the information on the label and the position 8 of the primary vessel 9 in the palette 17 are given.

Parallel to these operations, the requirement marking card 25 is fed into the card reader 26, and the information on this card is also read by the computer 23. The computer 23 controls the removal of the sample material 27, in accordance with the labeling 21 of the vessel and the information on the requirement marking card 25, from the primary vessel 9 in the removal position 8, after it has been rotated through 180° by the pipetting carriage 6 connected to the diluter 10, and the batches of sample are placed in the secondary vessel 12 for individual testing in accordance with the function of the requirement marking card 25.

Referring to FIGS. 3 to 6, these figures show the intermediate member constructed as gripping tongs 50, and the arrangement thereof and the connection to the clamping means 7 of the transporting carriage 6.

The gripping tongs 50 consist of an upper portion 51 and lower portion 52, the upper portion being fork-shaped and being positively locked in its end position by means of the area of the periphery of the closure member 40 which is uniformly bounded by the shoulder 43. The lower portion 52 has a recess 54 for the projection 44 on the closure member and in the center provides an opening 55 for the passage of the pourer nozzle 41. Connected to the lower portion 52 of the gripping tongs and pointing in the direction of the clamping means 7 of the transporting carriage 6, there is a lug 53 which can be inserted in a recess 7.1, this lug 53 having an air flow aperture 56 passing through the lug 53 as far as the area of the connection of the air feed pipe 42.

When the gripping tongs 50 are not inserted, the lug 53 is bent upwards, by means of a spring 53' inserted in the elastic material of the lug 53 and the lower portion 52 of the tongs to such an extent that the air flow aperture 56 is sealed off, and in some cases an articulated valve may be provided.

When the lug is pushed into the recess 7.1 and the lower portion 52 of the tongs is fixed by means of a position marking means 7.2, e.g. a step formed on the transverse arm 7.6, the air flow aperture 56 is opened and the air then flows through the air flow aperture 56 passing through the lug 53 and lower portion 52 of the tongs, into the connection for the air feed pipe 42, leading through the closure member 40 into the primary vessel 9. The air is supplied through an aperture 7.7 or the vertical arm thereof to the air connection (not shown) of the diluter 10. In the delivery position, the lower portion 52 of the tong is held by means of a magnetic connection 7.22 provided on the transverse arm 7.6 of the clamping means 7. The sample is delivered as explained with reference to FIG. 1. Positions 40 and 51 are secured in position by any desired means to prevent them from rotating relative to each other.

It may also be appropriate to provide an optical outflow monitoring device. In this case, it is advisable to provide optical carriers 7.4 designed to receive suitable monitoring means 7.5.

Figure 7:
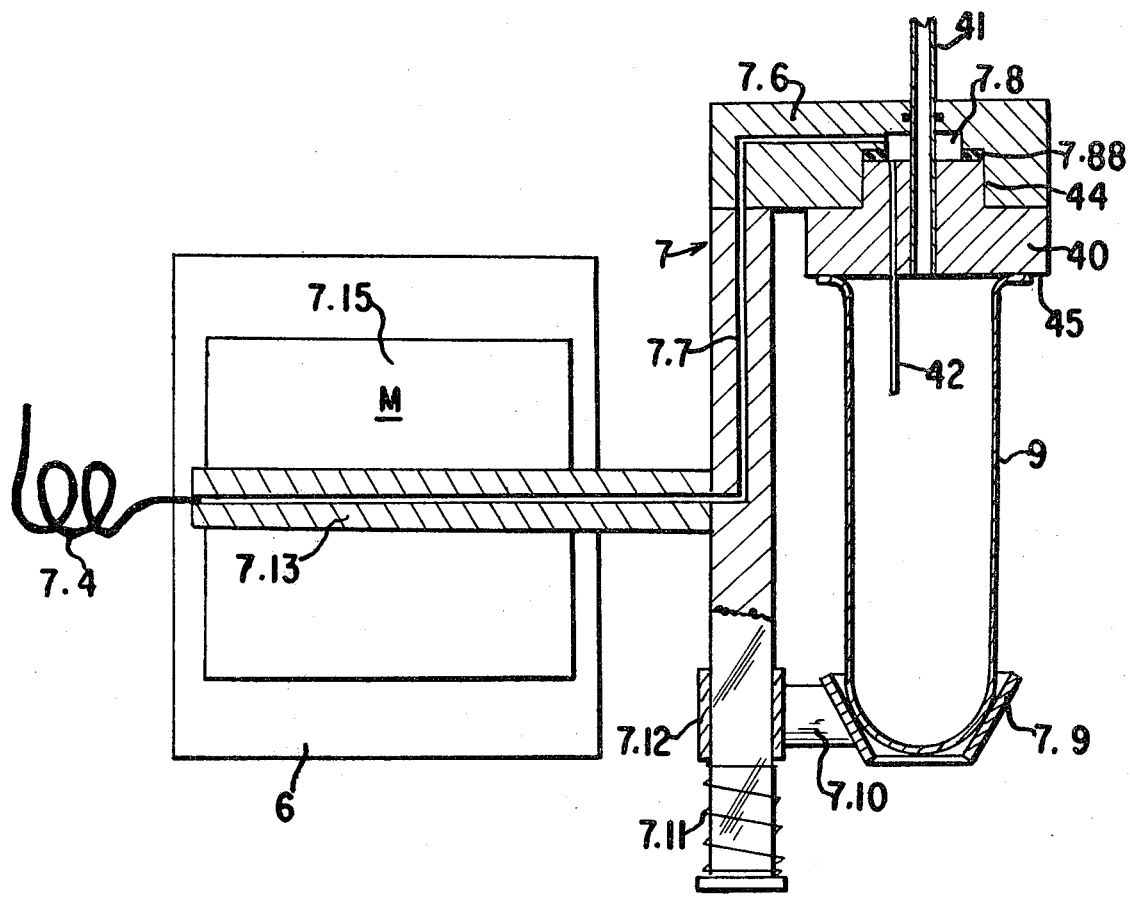
FIG. 7 shows the connection of the primary vessel to clamping means mounted on the transporting carriage and rotatable through 180° by a pivoting motor.

FIG. 7 shows an embodiment wherein, without the use of the intermediate carrier in the form of gripping tongs 50, the air passes directly through the clamping means 7, the transverse arm 7.6 thereof and the air aperture 7.7 into the recess 7.8 provided with a stop followed by 7.88 for the inserted portion 44 of the closure member 40. The stop makes it possible to provide an air space from which the air enters the primary vessel 9, directed towards the abutment portion 45, starting from the connecting port for the feed pipe 42, this port passing through the closure member 40.

The primary vessel 9 is held at the bottom by means of an inwardly conical hollow member 7.9 mounted on a transverse arm 7.10 of the clamping means 7 and movable thereon along a longitudinal guide 7.12, while a spring 7.11 presses the primary vessel 9, via the hollow member 7.9, against the abutment portion 45 of the closure member 40, so as to form a seal.

As in this example, the air aperture 7.7 may be connected to the diluter 10 via the pivot motor shaft 7.13 mounted in a stationary position on the clamping means 7, via a coil 7.14 which absorbs the pivoting movement and another line. The pivot motor 7.15 rotating through 180° is fixedly connected to the transporting carriage 6.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A method of sampling and distributing a liquid material which comprises drawing a liquid sample from a source thereof and placing it in a primary vessel, sealing said sample in the primary vessel with a sealing means which has one or more passages through which a positive pressure or a partial vacuum may be applied to the interior of the primary vessel and a relatively narrow dispensing passage from the interior of the primary vessel to the outside thereof, inverting the primary vessel containing the liquid therein by the combination of the sealing means, the walls of the vessel, the narrowness of the passage to the outside and by the equal or slightly negative pressure within the primary vessel with respect to the ambient pressure; moving the inverted primary vessel in a predetermined sequence to positions over secondary receiving vessels, increasing the pressure above the liquid in the primary vessel sufficiently to expel a predetermined amount of said liquid into a secondary vessel, reducing the pressure to equilibrium or to a slight vacuum, moving the primary vessel to successive positions and repeating the steps, recording data to relate the source of the sample in the primary vessel to the portions thereof dispensed into the secondary vessels and upon completing the desired providing of samples to various secondary vessels returning the primary vessel to its starting point.

2. A method as set forth in claim 1 wherein the changes in the position of the primary vessel are caused by moving it along the x-y axes in a plane above the plane in which the secondary receiving vessels are arranged.

3. A method of sampling and distributing a liquid material which comprises drawing a liquid sample from a source thereof and placing it in a stationary primary vessel positioned above secondary receiving vessels, sealing said sample in the primary vessel with a sealing means which has one or more passages through which a positive pressure or a partial vacuum may be applied to the interior of the primary vessel and a relatively narrow dispensing passage from the interior of the primary vessel to the outside thereof, inverting the primary vessel containing the liquid therein by the combination of the sealing means, the walls of the vessel, the narrowness of the passage to the outside and by the equal or slightly negative pressure within the primary vessel with respect to the ambient pressure; moving secondary receiving vessels to positions below the inverted primary vessel in a predetermined sequence, increasing the pressure above the liquid in the primary vessel sufficiently to expel a predetermined amount of said liquid into a secondary vessel, reducing the pressure to equilibrium or to a slight vacuum, moving the secondary vessels to successive positions and repeating the steps, recording data to relate the source of the sample in the primary vessel to the portions thereof dispensed into the secondary vessels.

* * * * *

UNITED STATES PATENT AND TRADEMARK OFFICE
CERTIFICATE OF CORRECTION

PATENT NO. : 4,413,060
DATED : November 1, 1983
INVENTOR(S) : GERD ASSMANN et al.

It is certified that error appears in the above-identified patent and that said Letters Patent is hereby corrected as shown below:

Title page: [73] should read:

-- Assignee: Boehringer Ingelheim Diagnostika GmbH, Munich, Fed. Rep. of Germany --

Signed and Sealed this

Twentieth Day of August 1985

[SEAL]

Attest:

DONALD J. QUIGG

Attesting Officer     Acting Commissioner of Patents and Trademarks